Figure 1:
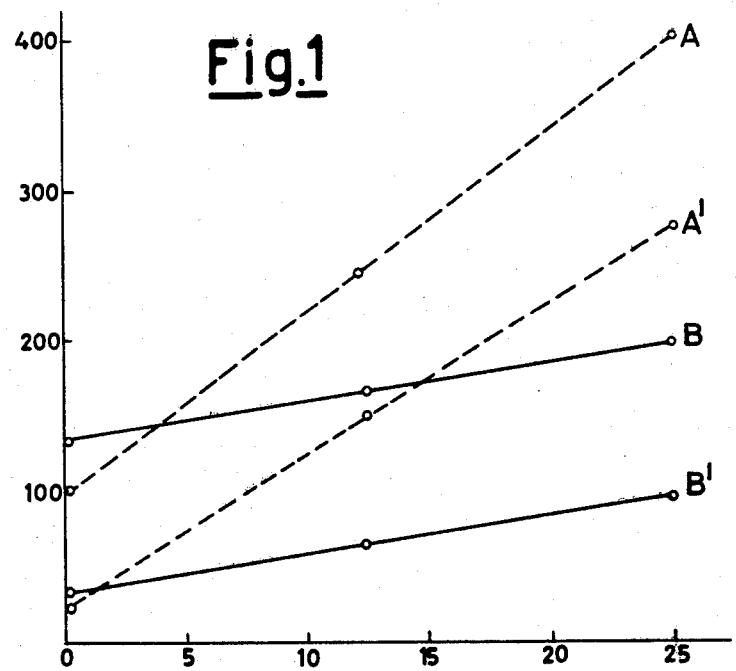

United States Patent [19]

Meiattini

[11] 4,254,220

[45] Mar. 3, 1981

[54] COMPOSITION FOR THE KINETIC DETERMINATION OF GLUCOSE

[75] Inventor: Franco Meiattini, Siena, Italy

[73] Assignee: Sclavo, S.p.A., Milan, Italy

[21] Appl. No.: 82,174

[22] Filed: Oct. 5, 1979

[30] Foreign Application Priority Data

Oct. 12, 1978 [IT] Italy .............................. 28665 A/78

[51] Int. Cl.³ ............................................. C12Q 1/54
[52] U.S. Cl. ......................................... 435/14; 435/28
[58] Field of Search ................................... 435/14, 28

[56] References Cited

U.S. PATENT DOCUMENTS

| | | | |
|---|---|---|---|
| 2,893,844 | 7/1959 | Cook | 435/14 |
| 3,886,045 | 5/1975 | Meiattini | 435/28 X |
| 3,964,870 | 6/1976 | Tiedemann | 435/14 |
| 4,098,574 | 7/1978 | Dappen | 435/14 |

*Primary Examiner*—Thomas G. Wyse
*Attorney, Agent, or Firm*—Morgan, Finnegan, Pine, Foley & Lee

[57] ABSTRACT

A composition for the determination of glucose in the kinetic mode comprising the enzymes glucose-oxidase and peroxidase, a buffer system, a component containing an aromatic ring with a phenolic hydroxyl attached to said ring, a component containing a reactive group containing a structure derived from 1-phenyl-5-pyrazolinone and a substance which inhibits glucose-oxidase but not peroxidase.

5 Claims, 4 Drawing Figures

COMPOSITION FOR THE KINETIC DETERMINATION OF GLUCOSE

This invention relates to a novel composition which is adapted to the kinetic determination of glucose.

From the U.S. Pat. No. 3,886,045 the possibility is known of enzymically determining glucose by using a particular assembly of reagents which exploits the transformation undergone by glucose in the presence of the glucose-oxidase enzyme, and the subsequent transitions which act upon the as-produced substances, first of all, among these, the oxidation, by the as-formed hydrogen peroxide, of an appropriate substrate under the action of the peroxidase enzyme.

The reactions which take place can be summarized as follows:

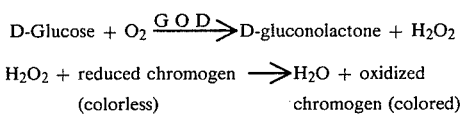

$$\text{H}_2\text{O}_2 + \text{reduced chromogen} \longrightarrow \text{H}_2\text{O} + \text{oxidized} \quad (2)$$
$$\text{(colorless)} \qquad\qquad\qquad \text{chromogen (colored)}$$

According to what has been disclosed in the above mentioned patent, in practice, a reagent GOD-POD-chromogen is used in the enzymic-colorimetric determination of glucose with a fixed-time spectrophotometric readout, or the readings are taken as the reactions involved have been completed.

Kinetic mode, as indicated herein, is, conversely, the measurement of the reaction velocity (V) in the portion of the reaction in which the reaction itself is of the zero order and V is a constant.

Usually, this method is used for measuring the enzymic activities with an excess of substrate; so that all the active sites of the enzyme are saturated and the reaction takes place at a constant initial speed.

The reaction velocity, under such conditions, is a function of the enzyme concentration exclusively.

The determination of the concentrations of the substrates, as in the case of glucose, can be made with difficulty in the kinetic mode because, in order that a zero order reaction may be obtained and to have the reaction under the conditions of constant reaction velocity, it is required, as outlined above, that all the active sites of the enzyme are constantly engaged, that is, it is necessary that an excess of substrate is present.

Inasmuch as in the analysis samples the concentration of the substrate varies from one sample to another and also in the same sample during progress of the reaction, it will be required that the enzymic activity is always very low, even relatively to the lowest concentration of substrate which might be found in the samples when the reaction has already taken place partially.

It is to be borne in mind that, in order that a reaction of zero order may be obtained, the substrate must always be in an excess relatively to the enzyme. Under such conditions, on account of the low enzymic activity which is present, any influence due to inhibitors, enzyme denaturation, temperature variations, activations and others, will have a considerable bearing on the reaction trend and consequently on the accuracy and reliability of the results.

The kinetic metering of the substrates is now made possible by resorting to trading-offs in the composition of the reagents and to technical and instrumental expedients.

As to the former, it is normal to decrease to appropriate levels the enzymic activity in the reagent; as to the latter, it is usual to resort to very short spectrophotometric readings which are carried out during the very first stage of the reaction, a stage which is nearly always linear, within a certain range.

This fact implies the adoption of automatic or semi-automatic instruments which are capable of taking the readings at very short time intervals which are rigorously constant: it is for these reasons that the kinetic mode methods for metering substrates can be used routinely only when appropriate apparatus are used, that which imposes not negligible limitations.

It has now been found that, which is the subject matter of this invention, a few substances introduced in the reagent for the colorimetric fixed-time determination of glucose, act as inhibitors of the glucose-oxidase, but do not so for peroxidase, so that such substances can be used to slow down the velocity of oxidation of the glucose in the reaction (1). Such a decrease of the reaction velocity seems to act on the complete system, as if the GOD enzyme was present in very low concentrations, or, conversely, as if the substrate (glucose) is in an excess relative to the enzyme: consequently, the reaction tends to become linear and its velocity tends to becoming constant.

Such velocity does not remain constant for a long time because the concentration of the substrate, obviously, tends to zero as the reaction concerned proceeds.

However, by acting upon the concentration of the added inhibitor, the time for the "reaction at constant velocity" becomes long enough as to permit that glucose may be determined in the kinetic mode also manually, that which, of course, does not exclude the use of automatic or semi-automatic instruments.

More particularly, thus, the present invention relates to a composition which is adapted to the determination, in the kinetic mode, of glucose, said composition comprising:
- glucose-oxidase and peroxidase enzymes
- buffer system
- a component containing in its molecule a ring having an aromatic character with at least an —OH group of the phenolic type
- a component containing a reactive group bonded to a structure deriving from 1-phenyl-5-pyrazolinone, and
- a substance which inhibits the activity of the glucose-oxidase enzyme.

Again, the composition according to the present invention can have the form of a single reagent, or it can comprise discrete mixtures of the various reagents to be combined at the instant of use. It lies within the expert to evaluate, in the preparatory stage, the advisability of using either form rather than the other one, and, at any rate, any choice will lie within the scope of the invention.

The substances which have been found to possess an inhibiting activity towards GOD and which can be used for slowing down the reaction velocity are: nitrates, thiocyanates (sulphocyanides), sulphites, selenites, semicarbazide.

These substances can be roughly divided into three groups, on the basis of their inhibiting power towards POD.

Group A: substances which do not inhibit POD (nitrates, selenites, sulphites).

Group B: substances which inhibit POD at concentrations higher than 0.1 M to 1 M (approx.) (thiocyanates).

Group C: substances which inhibit POD even at very low concentrations (between 0 and 0.1 M approx.) (semicarbazide).

The substances of the Group A can thus be used at any concentration which is judged appropriate to produce the expected inhibiting effect on GOD. The substances of the Group B can be used only at concentrations comprised between 0 and about 1 M. Finally, the substances of the Group C can be used only at concentrations comprised between 0 and 0.1 M approximately.

By so doing, the inhibition of the POD is always prevented, since the POD must not be influenced by the GOD inhibitor introduced in the reaction system.

By way of example, the use of ammonium nitrate in the Clu-Cinet is indicated.

Materials

1. Reagent GOD-POD-Chromogen (Glu-Cinet Scalvo) having the following composition (merely indicative without limitation)

| Phosphate buffer | 150 | millimol |
|---|---|---|
| GOD | 18 | units/milliliter |
| POD | 1 | unit/milliliter |
| 4-aminophenazone | 0.4 | millimol |
| 4-hydroxybenzoate | 10 | millimol |
| pH = 7.5 + 0.2 | | |

Note:
the pH may vary with the introduction of the inhibitor: with $NH_4NO_3$ (1-molar) the pH falls from 7.5 to 6.9, but the reagent operates satisfactorily in the kinetic mode also at that value of the pH. Thus, no correction is made for adjusting pH to the starting value provided that the variations do not overtake the boundary values 5.5 and 9.

2. $NH_4NO_3$ pure for analysis.

3. Standard solutions of pure glucose at various concentrations.

Methods

The reagent Glu-Cinet has been used as such, with additions (variable) of $NH_4NO_3$.

The procedure of use was as follows: to 2 mls of reagent are added 0.02 mls of a standard solution or of serum. After quick admixture, the measure of the reaction velocity is taken by using a photometer with automatic programmer and computer. During the analysis, the temperature is kept constant at the preselected value (such 30° C.).

Results (a) Duration of the linear period as a function of the concentration of the $NH_4NO_3$. As can be seen in the plot of FIG. 1, the linear period, for example with the glucose in the sample at 300 milligrams/deciliter passes, at 30° C. from about 35 seconds for $NH_4NO_3=0$ grams/deciliter to about 100 seconds for $NH_4NO_3=25$ grams/deciliter. At room temperature (22° C.), the transition is from about 25 seconds for $NH_4NO_3=0$ grams/deciliter to about 280 seconds for $NH_4NO_3=25$ grams per deciliter.

(b) Duration of the linear period as a function of concentration of glucose in the sample.

Figure 2:
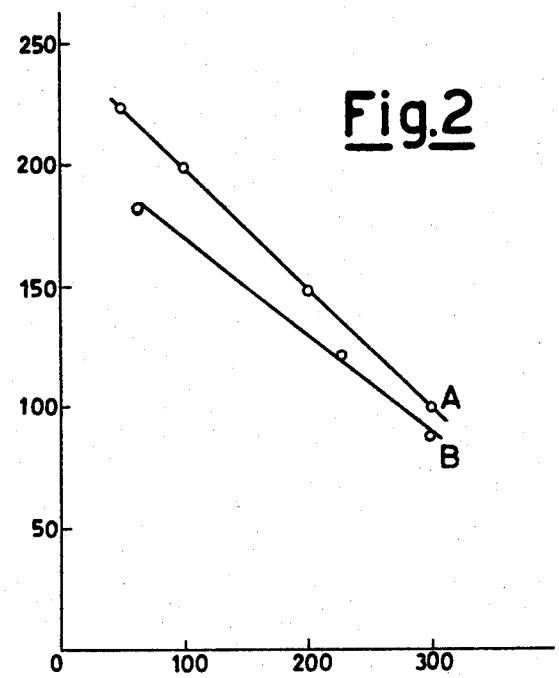

As can be seen in the plot of FIG. 2, the duration of the linear period is also a function of the concentration of glucose, and such duration is increased as the glucose concentration is decreased. At any rate, even with the glucose at 300 mg/dl in the sample and with $NH_4NO_3=12.5$ g/dl in the Glu-Cinet, the linear period has a duration of more that one minute and is thus sufficient to carry out the text in the kinetic mode conveniently and with a manual procedure.

(c) Response linearity

Figure 3:
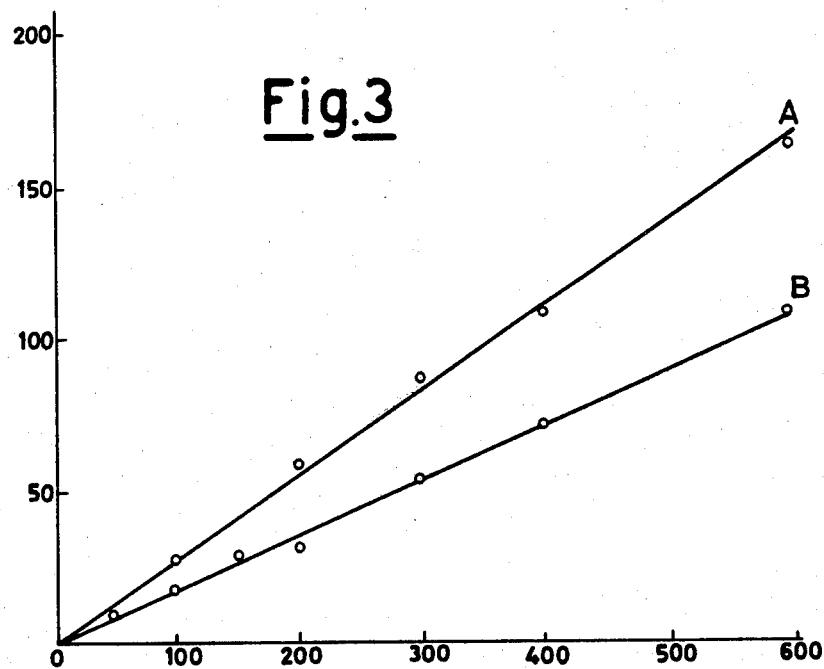

By carrying out the determinations on standard solutions of glucose having gradually increasing concentrations, there have been obtained response (reaction velocity vs. glucose concentration) which are linear up to 600 mg/dl of glucose in the sample both with $NH_4NO_3=12.5$ g/dl and with $NH_4NO_3=25$ g/dl in the Glu-Cinet (FIG. 3).

(d) Sensitivity

Figure 4:
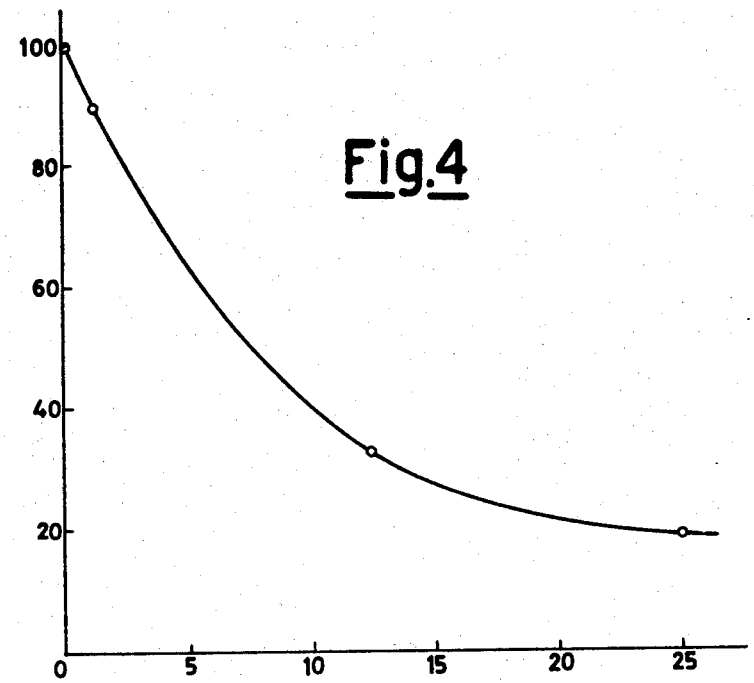

The sensitivity of the response (reaction velocity per concentration unit of glucose) is decreased, but not linearly, as the concentration of inhibitor in the reagent is increased, (FIG. 4). The concentration of the inhibitor is thus to be selected on the basis of the duration which is desired for the linear period, but still bearing in mind that too high concentrations of the inhibitor depress the sensitivity in an exceedingly strong manner.

Having reference to the drawings mentioned above, it is to be noted that:

The plot of FIG. 1 reports on the abscissae the concentration (g/dl) of $NH_4NO_3$ in the Glu-Cinet and, on the ordinates, the duration of the linear period (in seconds).

The curves A refer to a reaction temperature of 22° C., whereas the curves B refer to a reaction temperature of 30° C.

The curves A' and B' refer to a concentration of glucose in the sample of 300 mg/dl, whereas the curves A and B refer to a concentration of glucose in the sample of 100 mg/dl.

The plot of FIG. 2 reports the duration of the linear period (in seconds) as a function of the concentration of the substrate (abscissae): the linear period is extended as the concentration of glucose is decreased.

The curve A is with $NH_4NO_3=25$ g/dl and the curve B is with $NH_4NO_3=12.5$ g/dl of Glu-Cinet.

The plot of FIG. 3 reports the calibration curves (reaction velocity vs. concentration of glucose in the sample, on the abscossae), said curves being linear both with $NH_4NO_3=12.5$ g/dl (A) and with $NH_4NO_3=25$ g/dl (B).

Lastly, the plot of FIG. 4 reports on the abscissae the concentration of $NH_4NO_3$ in the Glu-Cinet and, on the ordinates, the relative sensitivity (in %). As can be seen the sensitivity is decreased, but not linearly, as the concentration of the inhibitor $NH_4NO_3$ is increased.

Conclusions

On the basis of the results which have been obtained, it has been ascertained that a satisfactory trade off between the duration of the linear period and the sensitivity, evaluated also for concentrations of different magnitude of the glucose in the sample, can be achieved by using the Glu-Cinet which contains $NH_4NO_3$ in concentrations variable in the range from 5 to 25 g/dl.

I claim:

1. A composition adapted for the kinetic determination of glucose, said composition comprising:
    (a) glucose-oxidase and peroxidase enzymes;
    (b) a buffer system;
    (c) a compound containing in the molecule an aromatic ring with at least a phenolic —OH;
    (d) a compound containing a group bonded to a 1-phenyl-5-pyrazolinone;
    (e) a substance for the inhibition of the glucose oxidase enzyme, said substance being selected from the group consisting of nitrates, selenites, sulphites, thiocyanates, and semicarbazide.

2. A composition as defined in claim 1 wherein the phenolic compound is 4-hydroxy benzoate.

3. A composition as defined in claim 2 wherein the compound containing a group bonded to a structure derived from 1-phenyl-5-pyrazolinone is 4-aminophenazone.

4. A composition as defined in claim 3 wherein the inhibitor substance is a nitrate.

5. A composition as defined in claim 4 wherein the inhibitor is ammonium nitrate.

* * * * *

UNITED STATES PATENT AND TRADEMARK OFFICE
CERTIFICATE OF CORRECTION

PATENT NO. : 4,254,220
DATED : March 3, 1981
INVENTOR(S) : Franco Meiattini

It is certified that error appears in the above—identified patent and that said Letters Patent is hereby corrected as shown below:

On the cover page, Assignee should be "Istituto Sieroterapico e Vaccinogeno Toscano "Sclavo" S.p.A., Siena, Italy".

Signed and Sealed this

Twenty-ninth Day of September 1981

[SEAL]

Attest:

Attesting Officer

GERALD J. MOSSINGHOFF

Commissioner of Patents and Trademarks